United States Patent [19]

Stokke et al.

[11] Patent Number: 5,005,655
[45] Date of Patent: * Apr. 9, 1991

[54] PARTIALLY HALOGENATED ETHANE SOLVENT REMOVAL OF OLEOPHYLIC MATERIALS FROM MINERAL PARTICLES

[75] Inventors: Olaf M. Stokke, Ponca City; David A. Flanigan, Cleveland, both of Okla.; Robert B. Ramsey, Wilmington, Del.; Robert E. Williams, Houston, Tex.; John Huycke, Ponca City, Okla.

[73] Assignee: Conoco Inc., Ponca City, Okla.

[ * ] Notice: The portion of the term of this patent subsequent to Jun. 6, 2006 has been disclaimed.

[21] Appl. No.: 330,392

[22] Filed: Mar. 28, 1989

Related U.S. Application Data

[63] Continuation-in-part of Ser. No. 104,858, Oct. 9, 1987, Pat. No. 4,836,302, which is a continuation-in-part of Ser. No. 937,557, Dec. 3, 1986, abandoned.

[51] Int. Cl.$^5$ .................. B01D 11/00; B08D 3/08; C09K 7/00; E21B 21/06
[52] U.S. Cl. .................. 175/66; 134/10; 134/40; 134/109; 210/634
[58] Field of Search .............. 175/66, 206; 252/8.51; 134/10, 13, 40, 109; 210/634

[56] References Cited

U.S. PATENT DOCUMENTS

| | | | |
|---|---|---|---|
| 3,688,781 | 9/1972 | Talley, Jr. | 175/208 |
| 3,693,733 | 9/1972 | Teague | 175/66 |
| 3,716,480 | 2/1973 | Finley et al. | |
| 4,027,731 | 6/1977 | Smith et al. | 166/267 |
| 4,040,866 | 8/1977 | Mondshine | 175/66 |
| 4,090,957 | 5/1978 | Leonard | 210/634 X |
| 4,120,775 | 10/1978 | Murray et al. | |
| 4,139,462 | 2/1979 | Sample, Jr. | 175/66 |
| 4,175,039 | 11/1979 | Fisher | 175/66 |
| 4,209,381 | 6/1980 | Kelly, Jr. | 175/66 |
| 4,304,609 | 12/1981 | Morris | 175/206 |
| 4,341,567 | 7/1982 | Roehl | 134/40 X |
| 4,395,338 | 7/1983 | Rowton | 175/66 |
| 4,411,074 | 10/1983 | Daly | 175/66 |
| 4,434,028 | 2/1984 | Eppig et al. | |
| 4,476,036 | 10/1984 | Figiel et al. | 134/40 X |
| 4,517,108 | 5/1985 | Hisamoto et al. | 134/40 X |
| 4,532,024 | 7/1985 | Haschke et al. | |
| 4,546,783 | 10/1985 | Lott | 175/66 |
| 4,606,283 | 8/1986 | DesOrmeaux et al. | |
| 4,645,608 | 2/1987 | Rayborn | 175/66 |
| 4,662,948 | 5/1987 | Weitzman | 134/25.1 |
| 4,683,963 | 8/1987 | Skinner | 175/66 |
| 4,816,174 | 3/1989 | Lund et al. | 134/40 X |
| 4,816,175 | 3/1989 | Lund et al. | 134/40 X |
| 4,836,302 | 6/1989 | Heilhecker et al. | 175/66 |

FOREIGN PATENT DOCUMENTS

| | | |
|---|---|---|
| 1019239 | 10/1977 | Canada . |
| 1115226 | 12/1981 | Canada . |
| 1172984 | 8/1984 | Canada . |

*Primary Examiner*—George A. Suchfield
*Attorney, Agent, or Firm*—A. Joe Reinert

[57] ABSTRACT

1,1-dichloro-2,2,2-trifluoroethane or 1,1-dichloro-1-fluoroethane are employed as solvents to remove oleophylic material from mineral particulates. In one aspect the method of this invention includes the steps of transporting oil-based mud-laden cuttings to a solid feed tank wherein the oil-based cuttings are subjected to turbulent mixing to leave the surface of the cuttings substantially free of oil. The cuttings are then subjected to countercurrent flow of solvent in order to separate oily solvent and fines smaller than a chosen diameter from the heavier solids. The heavier solids are cleaned of any remaining oil-based muds, separated from cleaning solvent and ultimately returned to the sea environment.

3 Claims, 1 Drawing Sheet

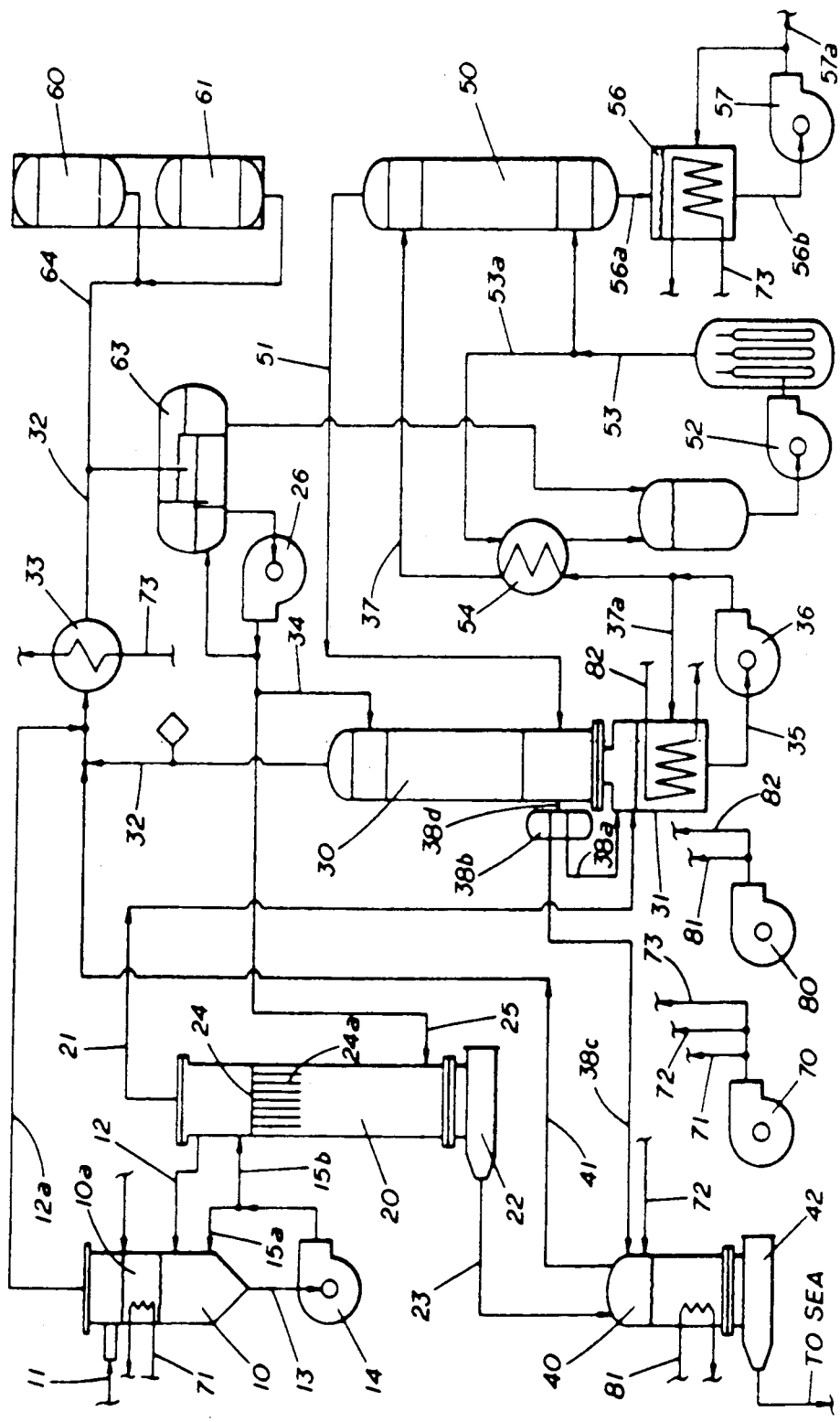

PARTIALLY HALOGENATED ETHANE SOLVENT REMOVAL OF OLEOPHYLIC MATERIALS FROM MINERAL PARTICLES

RELATION TO OTHER APPLICATONS

This application is a continuation-in-part of U.S. Pat. application No. 104,838, now U.S. Pat. No. 4,836,302, filed Oct. 9, 1987, entitled Apparatus and Method for Removing and Recovering Oil and/or Other Oil Based Drilling Mud Additives from Drill Cuttings, which in turn is a continuation-in-part of U.S. Pat. application Ser. No. 937,557, now abandoned, filed Dec. 3, 1986 and entitled Apparatus and Method for Removing Oil and/or Other Oil-based Drill Cuttings and Recovering Removed Oil or Other Additives.

FIELD OF THE INVENTION

The present invention relates to apparatus and method to remove oleophylic materials from mineral particles, particularly oil and/or other mud additives from the drill cuttings generated from downhole oil and gas drilling operations.

BACKGROUND OF THE INVENTION

In the drilling of oil and gas wells, drilling fluids or "muds" are used to provide well bore lubrication, to cool the drill bit, to protect against corrosion and to provide a pressure head to maintain formation integrity. There are two main types of drilling muds: water-based and oil-based. Oil-based drilling muds are employed in operations where it is desirable to drill at elevated temperatures, improve bore hole stability, control shale sloughing, and control water wetting of the formation such as in clay and some shale formations. Oil-based drilling muds are also desirable in "sour gas" wells where the water in a water-based drilling mud can react with the formation sulfur compounds and cause hydrogen embrittlement of the steels employed in the drilling operations. Oil-based drilling muds also inhibit corrosion and provide superior lubrication of the drill pipe in the well bore such as, for example, during directional drilling operations often conducted from offshore platforms.

Drilling muds are typically circulated down the inside of a tubular drill string, outwardly through the drill bit and up the annulus between the drill string and the bore. Drilling muds serve to carry the drill cuttings away from the bit and out of the bore hole. A typical oil-based drilling mud includes a diesel or mineral oil base, oil soluble emulsifiers, water (often salt water), oil wetting agents such as calcium sulfonates and organic amines to provide for oil wetting of the solids, and additives to control leak-off into the formation such as gilsonite and organophilic clays. The density of the drilling mud is adjusted with weighting agents such as barite or hematite. Oil-based drilling muds are very stable oil external/water internal emulsions including wetting agents to hold solids such as drill cuttings in the oil phase. The drill cuttings thus tend to become oil wet, trapping large quantities of oil-based mud in their intergranular spaces and creating environmental concerns regarding disposal of the contaminated drill cuttings.

For example, uncleaned drill cuttings which are dumped offshore can cause substantial pollution as the oil is gradually released from surface adhesion to the drill cuttings. Because the industry and the U.S. government want to avoid any such oil pollution, regulations governing the disposal of drill cuttings or solids have been promulgated.

In the prior art, drill cuttings contaminated with oil-based drilling muds were often collected in settling tanks where re-usable drilling mud was drawn off the top of the tank and contaminated drill cuttings, as bottoms, were transported to appropriate disposal sites. Such storage and transportation operations are costly and environmentally undesirable especially in offshore drilling operations. Typically, oil contaminated cuttings contain about fifty percent (50%) by volume of oil-based liquid. The value of this large volume of entrained oily liquids is considerable, and there is a strong economic incentive to recover the oil-based drilling mud both for economic as well as environmental reasons. Further, even burying of such oil-covered drill cuttings at waste disposal sites on shore is undesirable since the oil may eventually leach off the surface of the drill solids and enter subsurface water supplies.

In a more general outlook a need exists to remove oleophylic substances from mineral particles and soil or mud. For example, PCBs (polychlorinated biphenyl compounds) sometimes contaminate soils. Soils contain mineral particles such as sand, gravel, and the like as well as finer mineral particles such as silt, clay, loess and loam, which are referred to as mud herein when wet with water or an oleophylic liquid such as oil. Other contaminates can include waste oils, chloradane, etc.

For further example, it is also within the scope of the invention separate oleophylic substances from mineral particles and mud such as might be formed by grinding oil shale, tar sand, or the like. The oleophylic substances in this example can be kerogen, tar, or the like.

Several different methods for processing drill solids contaminated with oil-based mud have been attempted. For instance, U.S. Pat. Nos. 3,688,781; 3,693,733; 3,716,480; 4,175,039; 4,546,783 and 4,645,608 teach the use of aqueous solutions of detergents in an attempt to wash adsorbed oil-based mud from the surface of the drill cuttings. These methods have been largely unsuccessful because oil-based muds are specially formulated with powerful oil wetting agents that resist the detergent action of aqueous wash solutions. Additionally, detergent-laden water, which may be even more toxic to marine organisms than the oil on the drill solids, is continuously discharged into the marine environment.

U.S. Pat. Nos. 4,209,381 and 4,395,338 teach the use of steam to strip the more volatile oils from oily drill cuttings, followed in some cases by distillation of the cuttings to remove the higher boiling oil fractions. The methods are impractical offshore because of the excessively high energy requirements to generate the quantity of steam needed and the high temperatures needed to distill the oil.

U.S. Pat. Nos. 4,139,462; 4,304,609; 4,411,074 and 4,606,283 all teach various thermal methods to heat the oil-laden solids to drive off the oil as a vapor. Typically, the high temperatures required for these processes is supplied by electrical resistance heating, electrical induction heating, infra-red heaters, or high temperature heat transfer fluids. The methods have been at least partly unsuccessful for reasons already cited. The total amount of energy to heat all of the solids and boil all of the liquids off the cuttings is excessively high. Also, it is very dangerous to operate any equipment offshore in which hydrocarbon vapors are generated at temperatures well above their flash point.

U.S. Pat. No. 4,040,866 teaches the use of a mutual solvent to clean oily drill cuttings. A mutual solvent is one that is soluble in both oil and water. In this process, oily liquid is removed from the solids with a mutual solvent like ethylene glycol monobutyl ether; however, the mutual solvent remains on the cuttings and must be washed away with water leaving the cuttings free of oil and solvent. This method has proven impractical because two undesirable process streams are created. Large quantities of solvent (approximately equal to the original volume of oily liquid on the solids) are washed from the solids with water and discharged with the water into the environment. It is probable that the solvent is even more toxic to marine organisms than the oil which was removed from the cuttings. Additionally, large volumes of mutual solvent become contaminated with dissolved oil and must be either discarded or purified and recycled. The cost of mutual solvents prohibits simple disposal. Further, the high boiling point and high latent heat of vaporization of mutual solvents make their separation from oil by distillation difficult, expensive and hazardous.

U.S. Pat. No. 4,434,028 teaches a high pressure process for the use of a solvent which is miscible with oil but essentially immiscible with water to clean oily drill cuttings. In this process, a substance that is typically a gas at ambient temperature and pressure is compressed sufficiently to convert the gas to a liquid which then becomes a suitable solvent for the oil associated with drill cuttings. The liquified gas is then flowed, batchwise, through a vessel packed with oily solids. When the solids have been washed sufficiently clean, the chamber is depressurized allowing the solvent to flash into a vapor, leaving the solids free of oil and solvent. The oil-contaminated solvent can also be flashed to a vapor to separate it from the oil and allow it to be recycled. This process has not been successful on offshore drill sites for several possible reasons. High pressure is required to convert the normally gaseous material to a liquid so it can dissolve the oil on the solids. Mechanical problems associated with moving solids repeatedly into and out of high pressure vessels without leakage are formidable. Also, the batchwise nature of the process is not compatible with the continuous process of drilling and generation of drill cuttings. Finally, mechanical crushing of the cuttings prior to extraction requires heavy, bulky, maintenance-prone equipment which is especially undesirable for uses in offshore drilling operations.

SUMMARY OF THE INVENTION

In general, the present invention relates to a new method and apparatus for the separation of an oleophylic substance and mud from mineral particles contaminated with the oleophylic substance and mud. More particularly, the present invention relates to a new method and apparatus for the separation of oil-based drilling mud from drill cuttings and recovery of the drilling mud for reuse. The present invention employs a solvent which comprises at least one of 1,1-dichloro-2,2,2-trifluoroethane and 1,1-dichloro-1-fluoroethane. The solvent can also comprise mixtures of the two halogenated ethanes as well as mixtures of other substances such as alkanes, for example, having about five to about twelve carbon atoms per molecule. For many applications, however, only non-flammable solvents are suitable.

In one presently preferred mode, the method of this invention includes the steps of transporting oil-based mud-laden cuttings to a solid feed tank wherein the oil-based cuttings are subjected to turbulent mixing with solvent to dissolve the oil associated with the cuttings and leave the surface of the cuttings substantially free of oil. The cuttings are then transported to the countercurrent flow column and subjected to a countercurrent flow of clean solvent in order to separate oily solvent and fine solids smaller than a chosen diameter from the heavier solids. The heavier solids are cleaned of oil including oil previously trapped in the intergranular voids in the solids. The solids now containing solvent in the intergranular voids are subjected to heat to vaporize out the solvent leaving the cleaned solids to be returned to the sea environment. The oil-laden solvent from the separation column is thereafter distilled so that substantially pure solvent is removed from the mixture thus leaving a residuum of oil, fine solids and a small amount of solvent. The residuum is then subjected to steam stripping to remove substantially all of the remaining solvent thus leaving a substantially usable oil-based mud to return to the mud system. In this manner, the oil of the oil-based mud and other desirable fine particulate are removed from the cuttings so that the cuttings can be discharged to the sea environment and the oil-based mud and desirable solids be reused in the mud system for the oil well.

BRIEF DESCRIPTION OF THE DRAWINGS

The Figure is a partially schematic diagram illustrating the process and apparatus of a preferred embodiment of this invention. It is descriptive of the process and apparatus as applied to cleaning of oily drill cuttings, though it should be understood that the applicability is broader as is set out in the totality of this application.

DESCRIPTION OF THE PREFERRED EMBODIMENT

The apparatus of the presently preferred mode employed in practicing a method of one preferred embodiment is illustrated in the Figure. Basically, the apparatus includes a solids feed tank 10; a cleaning column 20; a bulk recovery or distillation column 30; a hot seawater tank 40; and, a stripping column 50. The apparatus further includes a solvent supply tank 60 and a solvent makeup tank 61. The utility water pump 70 is provided for pumping cooling water, which in the preferred embodiment of this invention is seawater at ambient conditions, to various vessels and locations to be further described later. A second general application pump 80 is provided to pump heated internal combustion engine or jacket coolant to various vessels and locations to be further described later.

Typically, the drill cuttings circulated through the mud system on an offshore oil well drilling platform are covered by oil-based drilling mud on all external surfaces and further have oil-based drilling mud trapped within the intergranular spaces or voids of the drill cuttings. The method and apparatus of this invention are provided for removing the oil-based drilling mud both from the surfaces and from the intergranular spaces of the drill cuttings. The principal cleaning solvent utilized in the process and apparatus of this invention comprises an effective amount of at least one of 1,1-dichloro 2,2,2-trifluoroethane ($CHCl_2CF_3$) and 1,1-dichloro-1-fluoroethane ($CCl_2FCH_3$) and is substantially miscible with oil and substantially immiscible with water. The particular solvents utilized in the preferred embodiment of this invention are preferably but not limited to solvents that are non-flammable and non-toxic so that their use on a drilling rig presents no safety concerns. The halogenated ethanes of this application are synthesizable by conventional means. They are also expected to be available from commercial sources such as E.I. Du Pont de Nemours and Company.

Referring to the Figure, a slurry of oil-based drilling muds and cuttings enters the apparatus of this invention through line 11. The drill cuttings in this slurry typically contain about 50% by volume of oil-based drilling mud absorbed within the intergranular spaces or voids of the drill cuttings. The drill cuttings may have already been subjected to some type of settling tank to allow some part of the oil-based drilling mud to separate by gravity from the drill cuttings in order to reduce the amount by volume of oil on the drill cuttings as described. However, it is within the scope of this invention to utilize the method and apparatus of this invention with oil-based drill cuttings which are taken directly out the mud-circulation system of the offshore drilling rig.

The drill cuttings enter through line 11 into the solids feed tank 10 and therein are subjected to a solvent washing action in order to remove substantially all of the oil-based drilling mud from the surface of the drill cuttings. The solids feed tank 10 also receives oil-laden solvent and fine solids recycled from the cleaning column 20 through line 12 which extends from the top of the cleaning column 20. The bottom outlet line 13 of the solids feed tank is attached to solid feed pump 14 which includes a recirculating line 15a and a transfer line 15b for transferring a slurry of oily solvent and washed drill cutting solids into the top of the cleaning column 20. The utility water or cooling pump 70 includes an output line 71 which circulates ambient seawater through heat exchange tubes in the solids feed tank 10 in order to cool a blanket of water, shown schematically as 10a, which in turn can cool the cuttings to a temperature below the boiling point of the solvent. Additionally, the cool water blanket will condense any solvent vapor that may be created by contact with inadequately cooled solids. Line 12a is a safety line in the event any solvent vapors escape the water blanket 10a. Line 12a connects to line 32 for recovery of clean solvent as will be later described. The contaminated drill cuttings are mixed with solvent in the solids feed tank and are stirred vigorously to create turbulent conditions to dissolve the oil associated with the drill cuttings. The stirring is accomplished by circulating the slurry of solvent and drill cuttings through pump 14 and returning the enhanced pressurized slurry through recirculating line 15a back into the solids feed tank 10. Other means of mechanical agitation to create turbulence may also be utilized. The turbulence is necessary to de-agglomerate the drill solids and to substantially wash the oily liquid from the surface of the drill cuttings or solids before the cuttings enter into the cleaning column 20. The amount of recirculation is controlled by valves in lines 15a and 15b or other suitable flow control means. Typically, about 80% of the solvent-solids slurry is recycled through the pump 14 in order to provide that the drill cutting solids are passed through the pump 14 about five times before entering line 15b to the cleaning column 20. This turbulent cleaning action is desirable because it ensures that the solid particles or cuttings are repeatedly subjected to high shear forces which enhance dispersion and inhibit agglomeration of the solid particles. High shear in the presence of a miscible solvent also assures that substantially all of the oil-based drilling mud is displaced from the surface of the cuttings and is dissolved in the solvent before the solids are sent through line 15b to the cleaning column 20. Thus the mixture of oily solvent and washed solids entering the cleaning column 20 through line 15b contain drill cuttings and solids which are substantially free of oil-based drilling mud at their surface so that further cleaning may be particularly directed to the easier task of removing the film of oily solvent and any remnants of oil-based mud from the surface of the cuttings. This operation can be performed under condition of substantially laminar flow.

Referring now to the cleaning column 20, outlet line 21 is attached to the top of the cleaning column to transfer oil-laden solvent, including fine solids from the drilling mud such as barite, organophilic clays and other desirable fine solids in addition to drill cutting fine solids. Line 21 transfers this slurry to an inlet into reboiler 31 attached to the bottom of the bulk recovery or distillation column 30.

A cleaning column transfer pump 22 is mounted onto the bottom of cleaning column 20 in order to transfer outwardly of the column through line 23 a slurry of solvent and substantially oil-free solids which enter into the top of the hot seawater tank 40.

The cleaning column 20 is a cylindrical vessel and includes a plate 24 having a plurality of downwardly extending tubular members 24a of a particular design diameter to be described. Clean solvent is fed continuously into the bottom of the cleaning column 20 through inlet line 25 which is also an output line for pump 26. As the solids rain downwardly in the upwardly flowing solvent within the cleaning column 20, the solids are progressively cleaned. As the liquid solvent flows upwardly through the cleaning column, it dissolves more and more oil and oily solvent off of the surface and out of the pores of the drill cuttings. Oil-free solids exit continuously from the bottom of the cleaning column 20 while the oil-laden solvent including fine solids in a mixture or slurry exit outwardly through outlet line 21. The cleaning column 20 provides a continuous countercurrent solvent extraction step employing the solvent of this application which is essentially completely miscible with oil and essentially immiscible with water. The countercurrent contact within the column 20 of the downwardly moving flow of solids with an upwardly moving stream of clean solvent is a preferred method for performing this step in the cleaning operation.

When the solvent-solids slurry enters the cleaning column through line 15b from the solids feed tank 10, the solids begin to fall or rain downwardly through the upwardly flowing solvent because of their greater density. Dirty carrier solvent mixes with the upwardly flowing clean solvent and both flow out of the top of the column. The solvent mixture exits as two separate streams 12 and 21 with identical composition. Stream or line 21 goes to reboiler 31 attached to the bottom of the bulk distillation column 30 where pure solvent is recovered for recycle. The second stream 12 flows back to the solids feed tank 10 to be reused as a wash and carrier solvent for the drill cuttings.

As the finely divided, solvent-washed solids fall downwardly through the cleaning column they are preferably made to pass through the one or more tubular orifices 24a which act as a solids classification zone. For a given cross-sectional area of the orifice tubes 24a, the upward countercurrent flow rate of clean solvent can be adjusted to give any desired upward linear velocity inside the orifices tubes. By proper selection of the upward velocity of solvent, one can cause particles smaller than a certain diameter to rise with the solvent while allowing particles larger than the critical size to fall against the upward flow of solvent.

The critical particle diameter which will be suspended by the rising liquid is determined by Stoke's Equation. This equation can be expressed as follows:

$$d^2(\text{crit}) = \frac{18\eta v}{g\Delta\rho}$$

where:
d = diameter of the particle in cm
$\eta$ = viscosity of the fluid in poises
v = velocity of the liquid stream in cm/sec
g = the acceleration of gravity in cm/sec$^2$
$\Delta\rho$ = difference in density between the solid particle and the moving liquid in grams/cm$^3$ The ability of the cleaning column 20 to separate solids according to their size is desirable because it allows one to force all the barite, organophilic clays, and other desirable fine solids, which make up an oil based mud, to flow out of the top of the column in line 21 to be recovered and recycled. The larger undesirable solids, now cleaned of oil-based drilling mud, are caused to flow out of the bottom of the cleaning column 20 in line 23 to the hot seawater tank 40 for subsequent discharge into the sea. Unlike other countercurrent washing processes where turbulence in the column is desirable to enhance washing action, turbulence in the cleaning column of this invention is undesirable and should be substantially avoided. Stokes Equation applies to particles moving in a stream of fluid in laminar flow. If turbulence is introduced into the column, the sharp separation of solids prescribed by Stokes Equation is compromised.

The oil solvent mixture containing fine solids smaller than some chosen diameter, such as about 40 microns for barite and 70 microns for drill solids, flow out of the top of the cleaning column 20 through line 21 and into reboiler 31 attached to the bottom of the distillation column 30.

The hot seawater tank 40 is an enclosed cylindrical vessel which receives the solvent and substantially oil-free solids from the cleaning column through cleaning column transfer pump 22. The hot seawater tank 40 is heated through line 81 extending from the heating water pump 80, which line 81 circulates through the hot seawater within the tank 40 in order to vaporize any remaining solvent associated with the cleaned drill solids. Such vaporized solvent exits the tank 40 through exit line 41 and connects into distillation column exit line 32. Makeup seawater is provided for the tank 40 through line 72 from utility water pump 70. The low boiling solvent associated with the cleaned solids is flashed in the hot seawater tank 40 thus leaving the cleaned drill cuttings or solids in hot seawater which is pumped outwardly by pump 42 to the sea. Thus the larger solids of the drill cuttings have now been discharged to the sea environment free of the oil-based drilling muds and solvent. The exiting vaporized solvent in line 41 joins with exiting vaporized solvent from distillation column line 32 to pass through a condenser 33 such that the condensed solvent enters clean solvent collection tank or accumulator 63. The cooling fluid for condenser 33 is provided through line 73 from the utility pump 70 which provides ambient seawater for condensing the vaporous solvent in line 32. Additional solvent is provided to line 32 and accumulator 63 through line 64 which extends from the solvent supply tank 60 and to the extent necessary from solvent makeup tank 61 to provide the necessary amount of cleaned solvent for the process. Solvent pump 26 pumps the clean solvent through line 25 to the bottom of the cleaning column 20 and through line 34 into the top of the distillation column 30.

The reboiler 31 is attached to the bottom of the distillation column 30 and contains heating coils through which hot jacket water is pumped from pump 80 through line 82. Heat from the hot jacket water is used to distill the solvent for recovery and reuse. The bulk recovery or distillation column 30 thus heats the oil-laden solvent containing fine solids received through line 21 from the top of cleaning column 20 to distill out of the slurry from line 21 solvent which exits through line 32 and is condensed in condenser 33 for collection in clean solvent collection tank 63 for subsequent reuse. A stream of residuum, containing oil-based mud and solvent exits outwardly of reboiler 31 through line 35 and is pumped by pump 36 through line 37 to the top of the stripping column 50. A recirculation line 37a is provided to recirculate any desired portion of the exiting residuum of oil-based mud and some solvent. Some of this water that is also vaporized in the reboiler 31 is internally condensed in column 30 and is withdrawn with some liquid solvent through line 38d to a standard solvent-water separator tank 38b where the two substantively immiscible liquids separate by difference in density so that the water is circulated into the hot seawater tank 40 through line 38c for ultimate discharge to the sea. Liquid solvent separated in 38b is recycled into the reboiler 31 through line 38a. Vaporized solvent also enters the bottom of the distillation column 30 from line 51 which is the exit line at the top of the stripping column 50 for returning any remaining vaporized solvent into the distillation column 30 for further purification and eventually for return and collection within the collection tank 63.

The purpose of the steam stripper column 50 is to remove any remaining amount of solvent within the oil-based mud and desirable fine solids exiting from line 35 of the reboiler 31. The stripping column 50 is heated by steam provided by steam generator 52 which provides steam to the bottom of the stripping column 50 through line 53. A branch line 53a of line 53 connects to a stripper preheater 54 for preheating the slurry of oil-based mud residuum and solvent before entering the stripping column 50.

A reclaim oil cooler 56 is attached to the bottom of the stripping column 50 and receives the oil-based mud and fines exiting through line 56a from the bottom of stripping column 50. Cooling water is provided through line 73 connected to the cooling water pump 70 in order to cool down the reclaimed oil-based drilling mud including desirable solids for return to the drilling mud system through pump 57. Pump 57 is connected to reclaimed oil cooler exit line 56b for transferring through pump output line 57a the reclaimed oil-based drilling mud and desirable solids back into the drilling mud system for reuse in drilling the well. By using greater or lesser amounts of steam provided by the steam generator 52, the concentration of solvent remaining in the oily mixture entering through line 37 can be reduced to any desired low value. After the steam stripping, the still bottoms exiting column 50 now have essentially the same composition as the liquid that contaminated the drill cuttings originally and may be recycled into the mud system for reuse. The vaporized solvent is returned from the stripping column 50 through line 51 to distillation column 30 for ultimate recycle in the continuous process of this invention.

The partially halogenated alkanes of the invention, 1,1-dichloro-2,2,2-trifluoroethane (HCFC-123) (CHCL2CF3) and 1,1-dichloro-1-fluoroethane (HCFC-141b) (CH3CCl2F) have surprisingly been shown to provide superior cleaning performance to provide clean mineral particles having greatly decreased toxicity to marine life, and to provide clean mineral particles having substantially less contamination with oleophylic substance (oil) when employed in accordance with our invention. Examplification follows:

1,1,2-trichloro-1,2,2-trifluoroethane (CFC-113) (CCL2FCCLF2) was originally favored as a solvent of choice to be employed in our process. It has many favorable characteristics including favorable solvent characteristics, boiling point, low toxicity, and the like. However, CFC-113 is a fully halogenated alkane and is not easily degraded by the forces of nature. Hence, recent evidence leaves the concern that this compound, being a fully halogenated alkane, may be a factor in degradation of the earth's ozone layer which provides a shield against ultraviolet radiation. For this reason, production of the compound is being phased out.

Because the HCFC-123 and HCFC-141b materials have at least one hydrogen molecule per molecule and are not fully halogenated, they are more easily broken down by the forces of nature. Thus, the HGFC-123 and HCFC-141b solvents are more readily eliminated from the atmosphere by degradation and pose a relatively low risk of potential damage to environment.

A number of other solvents have been considered. It turns out to be quite difficult to find a solvent having the proper combination of solvency, extractive ability, low toxicity, boiling point, and the like. It has been discovered that 1,1-dichloro-2,2,2-trifluoroethane and 1,1-dichloro-1-fluoroethane have suitable characteristics and surprisingly provide mineral particles (drill cuttings) having lower toxicity to marine life, provide superior cleaning performance, and provide superior solid/liquid separation as compared to CFC-113. Examplification follows:

A presently particularly preferred mode of the invention is in the extraction of oil from drill cuttings. Very low toxicity of the cleaned drill cuttings to marine life is demonstrated for both HCFC-123 and HCFC-141b solvents, which is surprisingly even lower than the toxicity of such drill cutting when extracted with CFC-113 solvent. In the offshore application of major current interest, the impact of the process cuttings on the marine environment is of great importance. The relative marine toxicity of oil based mud drill cuttings cleaned by CFC-113, HCFC-123, and HCFC-141b solvents, as determined by the EPA 1985 Drilling Fluids Test Protocol, was measured on simulated processed cuttings. The EPA test uses Mysidopsis bohia shrimp as a test species to determine a 96 hour $LC_{50}$ for the processed cuttings (mineral particles). The processed cuttings were simulated by contacting oil base mud drill cuttings with solvent in a stirred beaker for 8 minutes. The cuttings were recovered by decantation. Next, the cuttings were given a single contact wash with synthetic sea water at a temperature of 150° F. for 2 minutes (1 minute stirred, 1 minute quiescent) and then recovered by decantation. Results are presented in Table 1 below.

TABLE 1

| Sample | | $LC_{50}$, ppm |
|---|---|---|
| Raw Drill Cuttings | | 285 |
| Cuttings Processed with CFC-113 Solvent | | 13,480 |
| Cuttings Processed with HCFC-123 Solvent | | 27,316 |
|  | | 73,517 |
|  | Avg. | 50,416 |
| Cuttings Processed with HCFC-141b Solvent | | 111,371 |
|  | | 95,368 |
|  | Avg. | 103,369 |

Repetitive test were made with the HCFC-123 and HCFC-141b solvents. While the cuttings cleaned with the HCFC-123 solvent did not provide as good a result as those cleaned with the HCFC-141b solvent. Both solvents gave very good and acceptable results with average $LC_{50}$ values in excess of 30,000 ppm. The single test run with CFC-113 solvent gave results which were not acceptable.

Additionally, $LC_{50}$ test were run on sea water samples which had been mixed vigorously with CFC-113, HCFC-123, and HCFC-141b solvents at room temperature in separatory funnels and recovered by phase separation. When this procedure was carried out, all three sea water samples containing dissolved CFC-113, HCFC-123 and HCFC-141b solvent had $LC_{50}$ values of 1,000,000 ppm as shown in Table 2 below.

TABLE 2

| Sample | $LC_{50}$, ppm |
|---|---|
| Water Contacted with CFC-113 Solvent | 1,000,000 |
| Water Contacted with HCFC-123 Solvent | 1,000,000 |
| Water Contacted with HCFC-141b Solvent | 1,000,000 |

These results show that HCFC-123 and HCFC-141b solvents per se, when used for the purpose of cleaning cuttings do not harm the marine environment, as is true of CFC-113 solvent. Thus, both solvents of the invention appear to have very low or no marine toxicity.

Superior cleaning performance of the HCFC-123 and HCFC-141b solvents of the invention is also demonstrated with reference to the very effective CFC-113 in accordance with the following runs.

Samples of wellbore drill cuttings coated with oil mud (Batch A) were contacted with the three solvents using a mixture. After a fixed time, the mixing was stopped. The solvents were allowed to settle for 1 minute and a solvents laden sample was pipetted from the top of each mixture. These pipetted samples were centrifuged for solid/liquid separation observations as described in the series of runs which follows this series of runs. The solids were allowed to settle for approximately 15 hours. This separated the solids from the majority of the liquid. The liquid on top of the solvents was decanted and the jar containing the remaining solids and liquids was placed in a warm water bath to slowly evaporate the solvents.

The cuttings were then retorted to determine the amount of oil remaining on the cuttings. Table 3 shows the results for the CFC-113, HCFC-123 and HCFC-114b solvent runs. The HCFC-141b solvent left the least amount of oil on the cuttings at all the times tested. The HCFC-123 solvent also performed very well, being second best up to a mixing time of 15 minutes.

TABLE 3

| Mixing Time in Min. | Percent Oil, by weight, Left on Cuttings | | |
|---|---|---|---|
| | CFC-113 | HCFC-123 | HCFC-141b |
| 1 | 2.1 | 1.7 | 1.3 |
| 5 | 2.4 | 1.6 | 1.0 |
| 15 | 1.5 | 1.7 | 0.5 |

*Cuttings initially contained 13.5 percent oil by weight.

The cleaning performance of HCFC-141b solvent was clearly superior to that of CFC-113 solvent after the longer 15 minute run. However, the HCFC-123 solvent cleaned the cuttings better and more rapidly than the CFC-113 solvent for lower contact times.

In the runs described above, the solvent effectiveness was judged by the amount of residual oil left on the processed cuttings. In a separate series of runs that solvent effectiveness was judged by determining the weight of oil extracted by the solvent from the drill cuttings and calculating the amount of oil recovered as a percentage of the charged cuttings weight. Samples from a different batch of cuttings (Batch B) were contacted with solvent (5 mls per gm cuttings) by stirring in a beaker and then recovering by decantation. The recovered solvent was centrifuged to remove fines and then placed on a steam bath until the residue was nearly dry. The residue was dried in an oven and weighed to determine the amount of oil. The amount of oil removed from the cuttings was then calculated as a percentage of the cuttings weight. Results of these runs are shown in Table 4 below:

TABLE 4

| Mixing Time, min. | Oil Extracted from Cuttings, Wt. % | | |
|---|---|---|---|
| | CFC-113 | HCFC-123 | HCFC-141b |
| 5 | 8.23 | 8.44 | 9.62 |
| 150 | 8.15 | 8.05 | 10.50 |

The 5 and 150 minute tests were with separate samples. These results are in agreement and cumulative to those of this series of runs summarized in Table 3. Though the data show that the HCFC-141b solvent was the most effective, the HCFC-123 solvent was shown to be more effective than the CFC-113 solvent for shorter mixing times, as was the HCFC-141b solvent. After longer mixing times (2.5 hours) the CFC-113 and HCFC-123 solvents were comparable, which in itself is somewhat surprising since CFC-113 is an excellent solvent.

The foregoing series of runs clearly shows unexpected superior cleaning performance for the 1,1-dichloro-2,2,2-trifluoroethane and 1,1-dichloro-1-fluoroethane solvents of the invention.

The following series of runs demonstrates superior solid/liquid separation for the 1,1-dichloro-2,2,2-trifluoroethane and 1,1-dichloro-1-fluoroethane solvents of the invention.

The solvent laden samples removed after 1 minute of settling (Batch A runs in a series of runs above) were centrifuged for 10 minutes using a lab top centrifuge. Solids were centrifuged out of the liquid most easily with HCFC-141b solvent, then next most easily with the HCFC-123 solvent. The CFC-113 solvent had the poorest solvent separation of the three solvents. The CFC-113 and the solid slurry was translucent, but not clear. The HCFC-123 solvent and solid slurry was almost clear after centrifuging, but there were enough particles to slightly cloud the liquid. The HCFC-141b and solid slurry was clear after centrifuging. Close examination of the liquid indicated only a few widely spaced particles in the otherwise clear solution. Observations on centrifuging the solvents used in treating the Batch B cuttings confirmed that the HCFC-123 solvent had excellent solid separation relative to the CFC-113 solvent. However, after centrifugation, the HCFC-141b solvent was hazy, possibly as a result of doing a better job of extraction. Also, there were a few particles still suspended.

This series of runs shows a surprisingly superior solvent-liquid separation with the 1,1-dichloro-2,2,2-trifluoroethane and 1,1-dichloro-1-fluoroethane solvents of the invention as compared to CFC-113 solvent, which effects good separation in the process.

The runs presently made with the 1,1-dichloro-2,2,2-trifluoroethane and 1,1-dichloro-1-fluoroethane solvents of the invention indicate that a blend of the two solvents might be particularly advantageous in certain circumstances. For example, the aquatic toxicity test showed the cuttings processed with the HCFC-123 solvent were slightly more toxic than those processed with the HCFC-141b solvent. While the HCFC-123 solvent is non-flammable, the HCFC-141b solvent is regarded as flammable (Group D) at a concentration above about 6–15% in air. A blend of about ½ HCFC-123 solvent and ½ HCFC-141b solvent is non-flammable. Thus, a blend of HCFC-123 and HCFC-141b solvents is preferable to straight HCFC-141b solvent in terms of flammability and in many circumstances is preferable to straight HCFC-123 solvent in terms of toxicity of processed cuttings to marine life.

Particularly surprising is the demonstration of the runs that the HCFC-123 and HCFC-141b solvents are so superior to CFC-113 solvent in terms of aquatic toxicity of drill cuttings cleaned by these solvents. For example, CFG-113 solvent is generally regarded to be a very non-toxic substance with an exposure limit TLV value of 1,000 ppm. Also, CFC-113 solvent has a very low solubility in water of less than 200 ppm. Thus, those skilled in the art would conclude that the drill cuttings cleaned by CFC-113 solvent would give much better results on the $LC_{50}$ test, but surprisingly they did not. The HCFC-123 and HCFC-141b solvents would be expected to have lower exposure limits (TLV non determined) and higher solubilities in water. Yet, surprisingly, the drill cuttings cleaned by the HCFC-123 and HCFC-141b solvents gave extremely good results on the $LC_{50}$ test.

In certain applications, such as in a drill cuttings cleaning process where the solvent would in practical application be recovered by distillation, stabilization of the HCFC-123 and HCFC-141b solvents is advantageous. Compounds which can be employed for such stabilization include free radical scavengers. Effective concentrations can be used, for example on the order of about ½ percent.

It should be understood that the foregoing description and drawing of the invention are not intended to be limiting, but are only exemplary of the inventive features which are defined in the claims. For example, it is within the scope of this invention to utilize the method and apparatus of this invention for the removal of oil-soluble pollutants from contaminated soil such as might occur from leaking gasoline tanks, leaking PCBs from discarded transformers or leakage of other hazardous waste which are polluting the earth. In general, the process of this invention is well-suited for the removal of an oil soluble phase or oleophylic substance from intimate admixture with an oil insoluble phase such as mineral particles. For further example, the process may be used for the regeneration of activated charcoal or other adsorbents, the extraction of commercial entities from natural products such as vegetable oil from seeds, caffeine from coffee grounds and flavors and essences from plants. There are also circumstances in which water-based muds may be utilized in offshore or in other areas wherein the water-based muds contain oil added for lubricity. It is to be understood that the term "oil-based muds" as used herein includes such water-based muds having oil added for lubricity or for other reasons.

We claim:

1. A process for cleaning drilling mud containing an oleophylic substance from drill cuttings in order to prepare the cuttings for environmentally acceptable disposal, which comprises the steps of:
   (a) collecting drill cuttings which are contaminated with said drilling mud containing an oleophylic substance;
   (b) contacting the contaminated drill cuttings with a single solvent selected from 1,1-dichloro-2,2,2-trifluoroethane or 1,1-dichloro-1-fluoroethane to remove said drilling mud containing an oleophylic substance from the drill cuttings;
   (c) separating the drill cuttings from said solvent laden with said drilling mud containing an oleophylic substance to provide drill cuttings which are sufficiently free of solvent laden with said drilling mud containing an oleophylic substance for environmentally acceptable disposal;
   (d) moving the environmentally acceptable drill cuttings to the environment;
   (e) heating the solvent laden with drilling mud conaining an oleophylic substance to vaporize the solvent from the drilling mud containing an oleophylic substance;
   (f) recovering the drilling mud containing an oleophylic substance for further handling; and
   (g) condensing the vaporized solvent for recycle in the process by heat transfer with environmentally availble fluid at ambient temperatures.

2. A process according to claim 1 wherien the single solvent is 1,1-dichloro-2,2,2-trifluoroethane.

3. A process according to claim 1 wherein the single solvent is 1,1-dichloro-1-fluoroethane.

* * * * *